United States Patent
Olah et al.

(10) Patent No.: US 10,131,599 B2
(45) Date of Patent: Nov. 20, 2018

(54) FRACKING WITH CO$_2$ FOR SHALE GAS REFORMING TO METHANOL

(71) Applicant: UNIVERSITY OF SOUTHERN CALIFORNIA, Los Angeles, CA (US)

(72) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 216 days.

(21) Appl. No.: 15/036,506

(22) PCT Filed: Nov. 14, 2014

(86) PCT No.: PCT/US2014/065738
§ 371 (c)(1),
(2) Date: May 13, 2016

(87) PCT Pub. No.: WO2015/077153
PCT Pub. Date: May 28, 2015

(65) Prior Publication Data
US 2016/0340278 A1    Nov. 24, 2016

Related U.S. Application Data

(60) Provisional application No. 61/907,020, filed on Nov. 21, 2013.

(51) Int. Cl.
*E21B 43/26* (2006.01)
*C07C 29/00* (2006.01)
*E21B 43/267* (2006.01)
*C07C 1/24* (2006.01)
*C07C 41/09* (2006.01)
*C10L 1/04* (2006.01)
*E21B 43/16* (2006.01)
*E21B 43/34* (2006.01)
*E21B 43/40* (2006.01)

(52) U.S. Cl.
CPC .............. *C07C 29/00* (2013.01); *C07C 1/24* (2013.01); *C07C 41/09* (2013.01); *C10L 1/04* (2013.01); *E21B 43/164* (2013.01); *E21B 43/26* (2013.01); *E21B 43/267* (2013.01); *E21B 43/34* (2013.01); *C10L 2290/42* (2013.01); *E21B 43/40* (2013.01)

(58) Field of Classification Search
CPC ........ E21B 43/164; E21B 43/26; E21B 43/34; E21B 43/40; C07C 29/00; C07C 41/09; C07C 1/24; C10L 1/04; C10L 2290/42
See application file for complete search history.

(56) References Cited

U.S. PATENT DOCUMENTS

| | | | |
|---|---|---|---|
| 7,795,175 B2 | 9/2010 | Olah et al. | |
| 7,906,559 B2 | 3/2011 | Olah et al. | |
| 8,133,926 B2 | 3/2012 | Olah et al. | |
| 8,440,729 B2 | 5/2013 | Olah et al. | |
| 2007/0000666 A1 | 1/2007 | Vozniak et al. | |
| 2007/0261844 A1 | 11/2007 | Cogliandro et al. | |
| 2008/0296018 A1* | 12/2008 | Zubrin | C10G 1/04 166/267 |
| 2012/0067568 A1 | 3/2012 | Palmer et al. | |
| 2012/0115965 A1* | 5/2012 | Olah | C01B 3/38 518/704 |
| 2012/0118566 A1 | 5/2012 | Vandor | |
| 2012/0222422 A1 | 9/2012 | Nunley et al. | |
| 2013/0056205 A1 | 3/2013 | Carlson et al. | |
| 2013/0216460 A1 | 8/2013 | Ayasse et al. | |

FOREIGN PATENT DOCUMENTS

WO    2010/102971 A1    9/2010

OTHER PUBLICATIONS

International Search Report and Written Opinion, Appl. No. PCT/US2014/065738, dated Jan. 29, 2015.
International Preliminary Report on Patentability, Appl. No. PCT/US2014/065738, dated Oct. 22, 2015.
Bullis, "Shale Gas Will Fuel a U.S. Manufacturing Boom," Jan. 9, 2013, MIT Technology Review, Mar./Apr. 2013, 6 pgs.
Olah et al., "Bi-reforming of Methane from Any Source with Steam and Carbon Dioxide Exclusively to Metgas (CO—2H2) for Methanol and Hydrocarbon Synthesis," J. Am. Chem. Soc., 135:648-650 (2013).
Olah et al., "Single Step Bi-reforming and Oxidative Bi-reforming of Methane (Natural Gas) with Steam and Carbon Dioxide to Metgas (CO—2H2) for Methanol Synthesis: Self-Sufficient Effective and Exclusive Oxygenation of Methane to Methanol with Oxygen," J. Am. Chem. Soc., 137:8720-8729 (2015).

* cited by examiner

*Primary Examiner* — Brad Harcourt
(74) *Attorney, Agent, or Firm* — Winston & Strawn LLP

(57) ABSTRACT

A method of producing methanol from shale gas and CO$_2$ by the exclusive dry CO$_2$ fracking of shale rock by injection of gaseous CO$_2$ at a pressure between 10 and 100 atm to extract shale gas and recover it together with used CO$_2$; combining and admixing produced shale gas containing CO$_2$ and steam to produce a mixture of methane:carbon dioxide:water having a molar ratio of 3:1:2 for conducting the bi-reforming reaction to form a mixture of hydrogen and carbon monoxide having a molar ratio of 2:1 to 2.1:1; and converting the hydrogen and carbon monoxide under conditions sufficient to exclusively form methanol.

14 Claims, No Drawings

FRACKING WITH $CO_2$ FOR SHALE GAS REFORMING TO METHANOL

This application is a 371 filing of International patent application no. PCT/US2014/065738 filed Nov. 14, 2014, which claims the benefit of U.S. application No. 61/907,020 filed Nov. 21, 2013.

BACKGROUND

Recent discoveries and increasing production of shale gas represent a significant new source of natural gas (essentially methane) lasting well into the 21$^{st}$ century. The technology to produce shale gas from shale formations in various places generally utilize the procedure of hydrofracking by injecting large amounts of water under pressure containing potentially harmful chemicals that represent significant safety and environmental dangers and harm. Moreover, substantial quantity of water resources is required to effectively implement the procedure. There is a public outcry against the use of such a technology. Thus, various alternatives have been suggested.

US patent application publication 2013/0056205 discloses the use of argon as a supercritical fluid and proppant for fracking, but this involves use of a gel, foaming agent or other gas for successful delivery to the subterraneum formation.

US patent application publication 2012/0118566 suggests pumping metacritical phase natural gas to create or extend one or more fissures in a subterraneum formation for fracking. This is disclosed as being an improvement over hydraulic fracturing methods that use water, liquid nitrogen or liquid carbon dioxide, the latter of which is disclosed as requiring foaming agents. Furthermore, the used carbon dioxide would be released to the atmosphere where it can contribute to global warming or other harmful environmental conditions.

Rather than injecting water or liquids with added chemicals to release natural gas in the earth by fracturing the shale rocks an environmentally friendly procedure of "dry fracking" with pressurized carbon dioxide is now discovered. The underground shale rock formations are effectively cracked open by the pressurized gas. The advantage of "dry fracking" with compressed $CO_2$ is that the fracture pattern of the shale rock is more three dimensional, releasing more shale gas. The compressed $CO_2$ is many times less viscous than water. Furthermore, some of the used $CO_2$ for fracking is sequestered underground under pressure rendering the remaining shale more stable. As no water is used in dry fracking the environmental harm caused by hydrocracking is eliminated.

US patent application publication 2007/0261844 discloses a closed loop system for the capture and sequestering of carbon dioxide associated with the extraction of energy sources from large land masses. It suggests sequestering carbon dioxide in a shale reservoir or other formation. Sequestering of carbon dioxide, however, is not a viable solution for preventing the emission of carbon dioxide into the atmosphere, since the sequestration does not assure that the carbon dioxide will be maintained in the ground. The same is true of other forms of sequestration such as under the sea or in underground caverns.

$CO_2$ injection into depleting oil fields and gas wells is used to improve secondary oil and gas recovery. The use of $CO_2$ gas for fracking shale has not been utilized commercially and has been explored on a limited scale only. This technology was considered economically and technically impractical (see, e.g., K. Bullis, MIT Technology Review, Mar. 28, 2013).

In addition to using environmentally benign new fracking methods, there also is the need to convert shale gas to a convenient liquid fuel and chemical source material. The present invention avoids hydraulic fracking, as well as emitting carbon dioxide into the atmosphere while producing methanol providing an alternative general transportation fuel and chemical source material. It is thus a highly valuable process for replacing petroleum oil.

SUMMARY OF THE INVENTION

The invention relates to a method of producing methanol by obtaining shale gas and by using dry $CO_2$ fracking. The method involves dry fracking of shale rock by injection of gaseous $CO_2$ at a pressure of 10 to 100 atm to extract shale gas from its rock formations. The recovered shale gas is subsequently cleaned to remove contaminants including hydrogen sulfide and provide a clean shale gas comprising essentially methane and some of its homologues. Further steps include subsequent combining of the cleaned shale gas with $CO_2$ and water (steam) to produce a mixture of methane:carbon dioxide:water at a molar ratio of 3:1:2; conducting the bi-reforming reaction to form exclusively a mixture of hydrogen and carbon monoxide having a molar ratio of 2:1 to 2.1:1; and subsequently converting this mixture (metgas) under conditions sufficient to exclusively form methanol.

$CO_2$ from any available source is used for dry fracturing (fracking) of the natural gas containing shale formation. $CO_2$ is also separated from the liberated shale gas (methane) to provide $CO_2$ to be recycled to the injection step while part of the separated or accompanying $CO_2$ together with the needed amount of water (typically as steam) is used for the subsequent bireforming step. Injection $CO_2$ is produced from any natural or unnatural (industrial) source and is pressurized to the desired pressure of between 10 and 100 atm prior to injection into the shale rock. Energy needed for the bi-reforming reaction may be provided from any available energy source, including combustion of part of the methane from the recovered shale gas or from one or more alternative or green sources of energy.

The bi-reforming reactions are carried out over a catalyst at a temperature between about 800° C. and 1100° C. and a pressure of 5 to 40 atm, wherein the catalyst comprises V, Ti, Ga, Mg, Cu, Ni, Mo, Bi, Fe, Mn, Co, Nb, Zr, La or Sn, or oxides thereof in the form of a single metal catalyst, a single metal oxide catalyst, a mixed catalyst of a metal and a metal oxide, or a mixed catalyst of at least one metal oxide and another metal oxide, the catalyst optionally being provided on an oxide support. The produced metgas is directly converted to methanol.

The method can further comprise dehydrating all or a portion of the methanol to dimethyl ether (DME) and recycling the water from the dehydration step to the bi-reforming reaction. If desired, all or part of the dimethyl ether can be converted in the presence of a bifunctional (an acid-base) or zeolite catalyst under sufficient conditions to form ethylene and/or propylene.

The ethylene and/or propylene can be further converted under conditions sufficient to higher olefins, synthetic hydrocarbons, aromatics, or products produced therefrom, for use as a feedstock for chemicals or transportation fuels.

The invention also relates to various uses of the methanol that is formed from the methods disclosed herein. The methanol can be used as an essential economic and replenishable energy source material for conversion to hydrocarbon fuels, dimethyl ether or products derived from dimethyl ether. Methanol can also be used as a commonly useful fuel for internal combustion engines by admixing the methanol to or replacing gasoline or diesel fuel with methanol for combustion in modified or adjusted internal combustion engines.

DETAILED DESCRIPTION OF THE INVENTION

As noted, the present invention avoids the problems inherent with hydraulic fracking with water while also avoiding carbon dioxide emission into the atmosphere. Furthermore, an alternative energy fuel is provided by the present processes. These beneficial and unexpected advantages are achieved by utilizing shale gas containing $CO_2$ as a feed-stock to synthesize metgas ($2H_2$:CO) for methanol synthesis through the process of bireforming.

The present invention eliminates the use of hydrofracking with all its disadvantages and harm replacing it with "dry fracking" using $CO_2$. It involves the injection of pressurized $CO_2$ from any source through the borehole into the shale formations and recovering freed shale gas (methane) as well as using it together with $CO_2$ used for fracking. Part of the recovered $CO_2$ together with needed amount of steam is used for subsequent bireforming for metgas and thus methanol synthesis. This is the specific advantage of the presently disclosed dry fracking with $CO_2$ involving subsequent shale gas (methane) conversion to metgas through bireforming (U.S. Pat. Nos. 7,906,559; 8,133,926; 8,440,729 and *J. Am. Chem. Soc.* 2013, 135, 648-650) to produce methanol. It is an inventive, new, economical process of great significance to replace petroleum oil. It is a clean process with no by product or environmental harm.

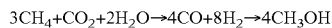

$$3CH_4 + CO_2 + 2H_2O \rightarrow 4CO + 8H_2 \rightarrow 4CH_3OH$$

Dry $CO_2$ fracking as stated eliminates environmental and safety problem caused by hydrofracking. Converting shale gas to liquid methanol through metgas makes it readily transportable and to be used as a transportation fuel for cars, modified diesel trucks and ships as well as a chemical raw material for derived products. The proposed method also mitigates the harmful effect of $CO_2$ emission into the atmosphere and eliminates contamination of subterranean water sources caused by hydrofracking significantly, "dry $CO_2$ fracking" followed by methanol synthesis also provides a solid economic basis for the overall process.

An alternative renewable source to replace oil is essentially needed. Our petroleum oil reserves are depleting and are fully utilized by increasing demands of a growing population for transportation fuels and chemical raw materials. Natural gas has already become significant in essentially replacing oil in electricity generation while more abundant coal still maintains a key role. These resources, however, are also not limitless. Extensive discoveries of shale gas with improved fracking methods, such as dry fracking will extend the availability of natural gas to replace oil. They offer humankind an extended period of assured reserves reaching into the next century allowing development of alternate energy sources and safer atomic energy.

The present invention discloses a feasible and economic way to replace hydrofracking, which uses very large amounts of water and harmful chemicals with dry $CO_2$ gas fracking. It also allows ready liquefaction of produced shale gas to methanol for replacing oil as a convenient liquid transportation fuel and chemical source material.

Capturing carbon dioxide emissions from biological and natural sources is carried out in nature's photosynthetic recycling, but increased anthropogenic release of $CO_2$ into the atmosphere since the dawn of the industrial revolution is continuing to overload nature's recycling ability. This contributes to harmful ocean acidification as well as increased global warming. It represents a challenge for humankind to mitigate and chemically recycle excess $CO_2$. The only developed technology until now is carbon capture and sequestration (storage) CCS, which is however an expensive and only a temporary solution. Mineralization as well as conversion of underground or deep-sea stored $CO_2$ to carbonate rocks is a very slow process for which we hardly can wait. In contrast, the capture and chemical recycling of $CO_2$ (CCR) represent a feasible and economic solution under the right conditions.

The first step of the method involves injecting pressurized carbon dioxide from any source into the shale formation resulting in fracture and displacing the trapped gas and allowing it to be recovered through the borehole. The $CO_2$ gas pressure is generally between 10 to 100 atm, which can easily be attained with the use of conventional compressors, pumps and piping equipment. If needed, injection equipment can also be used to introduce with the dry $CO_2$ gas a solid particulate propping material such as sand (see, e.g., US patent application publication 2007/0000666). No chemical additives are needed as the pressurized injection of $CO_2$ alone is sufficient to achieve fracking. The bulk of the injected $CO_2$ is recovered from the produced shale gas and can be recycled for the fracking process. Part of it, however, can be retained in the extracted shale rock rendering it more stable and providing permanent safe sequestration.

The liberated mixture of shale gas and used $CO_2$, after purifying it mainly to remove hydrogen sulfide and other impurities, is then adjusted with the addition of water (generally as steam) to obtain a mixture of methane, $CO_2$ and steam in 3:1:2 molar ratio to form the needed fuel for the bireforming step and subsequent methanol synthesis using a mixture of CO and hydrogen in 1:2 molar ratio. The purification steps are known and practiced in existing natural gas production. Hydrogen sulfide is removed to avoid also catalyst poisoning. The removed hydrogen sulfide can be converted to elemental sulfur or non-toxic sulfur compounds, which can be recovered or discarded (see for example, US patent application publication 2013/0216460).

The bireforming step is described in US patent application publication 2012/0115965. Typically, the bireforming reaction is conducted by passing the gas mixture over a catalyst, such as the catalysts disclosed in the US patent publication, and at a temperature between about 800° C. and 1100° C., preferably from about 800° C. to about 850° C., and a pressure of 5 to 40 bar sufficient to produce metgas, namely a syn-gas mixture of carbon monoxide/hydrogen ($CO/H_2$) in a molar ratio of about 2:1, preferably between 2:1 and 2.1:1, and most preferably about 2.05:1; and subsequently further sufficient combination to convert such mixture of $H_2$ and CO exclusively to methanol, as follows:

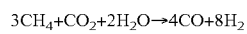

$$3CH_4 + CO_2 + 2H_2O \rightarrow 4CO + 8H_2$$

which then results in the further transformation: $4CO + 8H_2 \rightarrow 4CH_3OH$.

To carry out the bi-reforming reaction, a catalyst or combination of catalysts are to be used. These catalysts include any suitable metal or metal oxide, including without limitation a metal such as V, Ti, Ga, Mg, Cu, Ni, Mo, Bi, Fe, Mn, Co, Nb, Zr, La or Sn, and corresponding oxides of such metals. These catalysts may be used as a single metal, or a combination of a metal and metal oxide, or a combination of metal oxides, supported on a suitable support such as a high surface area nanostructured oxide support such as fumed silica or fumed alumina. By way of example, NiO, metal-metal oxides such as Ni—$V_2O_5$, $M_2O_3$—$V_2O_5$, and NiO—$V_2O_5$, as well as mixed oxides such as $Ni_2V_2O_7$ and $Ni_3V_2O_8$ can be used. The preferred catalysts include Cu/ZnO catalysts and the bireforming reaction is conducted at atmospheric pressure in a flow reactor at a temperature between 220 to 250° C. One skilled in the art would appreciate that a number of other related metal and metal oxide catalysts, and their combinations, can also be used. Needed suitable reactors for the conversion reactions as well as pressurized continuous flow reactors are well known and commercially available.

The necessary carbon dioxide for the dry fracking process can be obtained from any available natural or industrial sources such as carbon fuel burning power plants, chemical plants, cement plants, etc. The needed new infrastructure essentially involves only $CO_2$ pipelines from various industrial $CO_2$ producing sources or natural sources. The $CO_2$ used in the dry fracking is captured, separated and recycled. Some of the $CO_2$ as mentioned is utilized in the bireforming process. The only use of water in the overall process is the stoichiometric amount of steam needed in the bireforming unit for subsequent metgas synthesis. This eliminates the potential harmful environmental and geological effects of the use of water in hydrofracking.

A further significant aspect of our invention is that the safely and efficiently prepared methanol from abundant shale gas sources using the disclosed process can be used to prepare methanol as the common fuel for all internal combustion engines (including modified diesel vehicles, maritime vessels, trains, military vehicles, etc.) replacing oil and its products. This eliminates presently needed separate infrastructures and transportation (storage) systems for gasoline and diesel fuel using vehicles. Advances in modified diesel engines developed recently at MIT (K. Bullis, MIT Technology Review, Mar. 28, 2013) allow the use of methanol as a common fuel for all (ICE) internal combustion engines. This allows use of common storage transportation and distribution systems representing fundamental simplicity of great economic value. Further, if needed, methanol can also be readily converted into conventional hydrocarbon (including diesel) fuels and derived chemical products using the Exxon-Mobil zeolite of Olah et. al., supported bifunctional acid-base catalyst based systems (G. A. Olah and A. Molnar, "Hydrocarbon Chemistry", $2^{nd}$ ed., 2004, Wiley and references therein) replacing petroleum oil and dependence on oil monopolies.

EXAMPLES

The following examples illustrate the preferred embodiments of the invention without limiting them.

Example 1

The dry fracking of shale gas with pressurized $CO_2$ is carried out by injecting pressurized (10-100 atm) $CO_2$ through the borehole involving both vertical and horizontal sections for fracking the shale formation and releasing the liberated shale gas containing methane together with the added $CO_2$.

Example 2

A shale gas (natural gas) $CO_2$ mixture obtained from $CO_2$ dry fracking process is purified from hydrogen sulfide, adjusted with addition of $CO_2$ and steam to obtain a molar ratio 3:1:2 of methane, $CO_2$ and steam, which upon reforming process in a flow reactor over a catalyst such as NiO at a temperature of about 800° C. to 1100° C., preferentially between 800-850° C. yields metgas. Suitable catalysts include other varied metal and metal oxides such as V, Ti, Ga, Mg, Cu, Ni, Mo, Bi, Fe, Mn, Co, Nb, Zr, or Sn used as single metal, metal oxides or their combination. They can be supported on suitable support, preferentially suitably large nanostructured surface such as fumed silica or aluminum. A preferred catalyst is NiO on fused alumina support or a CU/ZnO catalyst. This process provides a mixture that only contains CO and $H_2$.

Example 3

Hydrogen and carbon monoxide produced in approximately 2:1 ratio are converted to produce methanol under catalytic reaction conditions using usual copper and zinc oxides and related catalysts.

Example 4

Methanol produced in Example 3 is dehydrated to dimethyl ether using a solid acid catalyst such as Nafion H between 100° C. to 200° C.

Example 5

The water formed during dehydration of methanol to dimethyl ether is recycled to be used in the bi-reforming reaction in Example 1.

The invention described and claimed herein is not to be limited in scope by the specific embodiments herein disclosed, as these embodiments are intended as illustrative of several aspects of the invention. Any equivalent embodiments are intended to be within the scope of this invention, as they will become apparent to those skilled in the art from the present description. Such embodiments are also intended to fall within the scope of the appended claims.

Finally, all patent applications mentioned herein in the detailed description are expressly incorporated herein by reference thereto.

What is claimed is:

1. A method of producing methanol by obtaining a shale gas and $CO_2$ mixture from exclusive dry $CO_2$ fracking, which comprises:
   dry fracking of an underground shale rock formation by injection of dry, gaseous $CO_2$ into the shale rock at an injection pressure of between 10 and 100 atm to cause fracking of the rock and subsequently generate a shale gas mixture comprising methane, carbon dioxide and contaminants;
   recovering the shale gas mixture from the fracked shale rock and separating it for $CO_2$ to be recycled with cleaning to remove $CO_2$ and contaminants including hydrogen sulfide and provide a cleaned shale gas mixture consisting essentially of methane;
   combining the cleaned shale gas mixture with recycled $CO_2$ that is recovered from dry fracking and $H_2O$ in amounts sufficient to produce a mixture of methane: carbon dioxide:water at a molar ratio of 3:1:2;

conducting a single-step bi-reforming reaction with the methane:carbon dioxide:water mixture to form only carbon monoxide and hydrogen as follows:

$$3CH_4+CO_2+2H_2O \rightarrow 4CO+8H_2$$

in a mixture having a molar ratio of hydrogen and carbon monoxide of 2:1 to 2.1:1; and converting the mixture of hydrogen and carbon monoxide under conditions sufficient to exclusively form methanol, as follows:

$$4CO+8H_2 \rightarrow 4CH_3OH.$$

2. The method of claim 1, wherein the $CO_2$ for dry fracking is derived from any natural or industrial source and is pressurized to the injection pressure prior to injection.

3. The method of claim 2, wherein the derived $CO_2$ is pressurized, generally between 10 and 100 atm prior to injection into the shale rock.

4. The method of claim 1, which further comprises providing needed energy for the bi-reforming reaction from combustion of part of the methane from the recovered shale gas or from one or more renewable sources of energy or atomic energy.

5. The method of claim 1, wherein the bi-reforming reactions are carried out over a catalyst at a temperature between about 800° C. and 1100° C. and a pressure of 5 to 40 atm, wherein the catalyst comprises V, Ti, Ga, Mg, Cu, Ni, Mo, Bi, Fe, Mn, Co, Nb, Zr, La or Sn, or oxides thereof in the form of a single metal catalyst, a single metal oxide catalyst, a mixed catalyst of a metal and a metal oxide, or a mixed catalyst of at least one metal oxide and another metal oxide, the catalyst optionally being provided on an oxide support.

6. The method of claim 1, wherein the molar mixture of hydrogen and carbon monoxide is present at a molar ratio of approximately 2.05 to 1 for subsequent methanol synthesis.

7. The method of claim 1, which further comprises dehydrating all or a portion of the methanol to dimethyl ether and water and recycling the water from the dehydration to the bi-reforming reaction.

8. The method of claim 7, which further comprises converting the dimethyl ether in the presence of an acid-base or zeolite catalyst under conditions sufficient to form one of ethylene propylene.

9. The method of claim 8, which further comprises converting either the ethylene or propylene under conditions sufficient to form higher olefins, synthetic hydrocarbons, aromatic compounds, or a product produced from the foregoing.

10. A method of providing an essential economic and replenishable energy source material which comprises:

obtaining methanol from the method of claim 1; and
converting the methanol to a hydrocarbon fuel, dimethyl ether or products derived from dimethyl ether.

11. A method of providing a commonly useful fuel for internal combustion engines, which comprises:

obtaining methanol from the method of claim 1; and
admixing the methanol to or replacing gasoline or diesel fuel with methanol for combustion in modified or adjusted internal combustion engines.

12. The method of claim 1, which further comprises converting the methanol as an essential economic and replenishable energy source material to hydrocarbon fuels, dimethyl ether or products derived from dimethyl ether.

13. The method of claim 1, which further comprises preparing a commonly useful fuel for internal combustion engines by admixing the methanol to or replacing gasoline or diesel fuel with methanol for combustion in modified or adjusted internal combustion engines.

14. A method of producing methanol by obtaining a shale gas and $CO_2$ mixture from exclusive dry $CO_2$ fracking, which comprises:

dry fracking of shale rock by injection of gaseous $CO_2$ into the shale rock at an injection pressure of between 10 and 100 atm to cause fracking of the rock and generate a shale gas mixture;

recovering the shale gas mixture from the fracked shale rock and separating it for $CO_2$ to be recycled with cleaning to remove $CO_2$ and contaminants including hydrogen sulfide and provide a cleaned shale gas mixture consisting essentially of methane;

combining the cleaned shale gas mixture with recycled $CO_2$ that is recovered from dry fracking and $H_2O$ in amounts sufficient to produce a mixture of methane:carbon dioxide:water at a molar ratio of 3:1:2;

conducting a single-step bi-reforming reaction with the methane:carbon dioxide:water mixture to form only carbon monoxide and hydrogen as follows:

$$3CH_4+CO_2+2H_2O \rightarrow 4CO+8H_2$$

in a mixture having a molar ratio of hydrogen and carbon monoxide of 2:1 to 2.1:1; and converting the mixture of hydrogen and carbon monoxide under conditions sufficient to exclusively form methanol, as follows:

$$4CO+8H_2 \rightarrow 4CH_3OH,$$

wherein methanol is synthesized over Cu/ZnO catalysts and the bireforming reaction is conducted at atmospheric pressure in a flow reactor at a temperature between 220 to 250° C.

* * * * *